(12) United States Patent
Pachur et al.

(10) Patent No.: US 8,551,987 B2
(45) Date of Patent: Oct. 8, 2013

(54) CRYSTALLINE ETHYL 4-[4-[(2R)-3-[4-AMINO-3-CHLORO-5-(TRIFLUOROMETHYL)PHENYL]-1-OXO-2-[[[4-(1,2,4,5-TETRAHYDRO-2-OXO-3H-1,3-BENZODIAZEPIN-3-YL)-1-PIPERIDINYL]CARBONYL]OXY]PROPYL]-1-PIPERAZINYL]-PIPERIDINE-1-ACETATE DIFUMARATE

(75) Inventors: Kathrin Pachur, Schwendi (DE); Uwe Joerg Ries, Biberach (DE); Ulrike Werthmann, Biberach (DE); Sonja Sproll, Steinhausen a.d. Rottum/Englisweiler (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 213 days.

(21) Appl. No.: 12/680,060

(22) PCT Filed: Sep. 25, 2008

(86) PCT No.: PCT/EP2008/062847
§ 371 (c)(1),
(2), (4) Date: Sep. 14, 2011

(87) PCT Pub. No.: WO2009/043797
PCT Pub. Date: Apr. 9, 2009

(65) Prior Publication Data
US 2012/0058994 A1 Mar. 8, 2012

(30) Foreign Application Priority Data
Sep. 28, 2007 (DE) .......................... 10 2007 046 888

(51) Int. Cl.
*C07D 401/14* (2006.01)
*A61K 31/551* (2006.01)
(52) U.S. Cl.
USPC .......................................... 514/221; 540/500
(58) Field of Classification Search
USPC .......................................... 540/500; 514/221
See application file for complete search history.

(56) References Cited

U.S. PATENT DOCUMENTS

2007/0049581 A1    3/2007 Mueller et al.

FOREIGN PATENT DOCUMENTS

| CA | 2618834 A1 | 2/2007 |
|---|---|---|
| WO | 2007020261 A2 | 2/2007 |

OTHER PUBLICATIONS

Gould; Salt selection for basic drugs; International Journal of Pharmaceutics; Nov. 1, 1986; vol. 33; pp. 201-217.
International Search Report, Form PCT/ISA/210, for corresponding PCT/EP2008-062847; May 25, 2009.
Stahl et al., The Practice of Medicinal Chemistry; 35 Preparation of water-soluble compounds through salt formation, 2003, pp. 601-615.
*Pfizer, Inc. v. Apotex, Inc.*, 480 F.3d 1348 (Fed. Cir. 2007).

Primary Examiner — Bruck Kifle
(74) Attorney, Agent, or Firm — Michael P. Morris; Alan R. Stempel

(57) ABSTRACT

The invention relates to the novel salts AB of the base A with a physiologically acceptable acid B which is selected from the group consisting of hydrochloric acid, hydrobromic acid, sulfuric acid, fumaric acid and salicylic acid and the polymorphic compounds, the corresponding solvates and hydrates thereof.

(A)

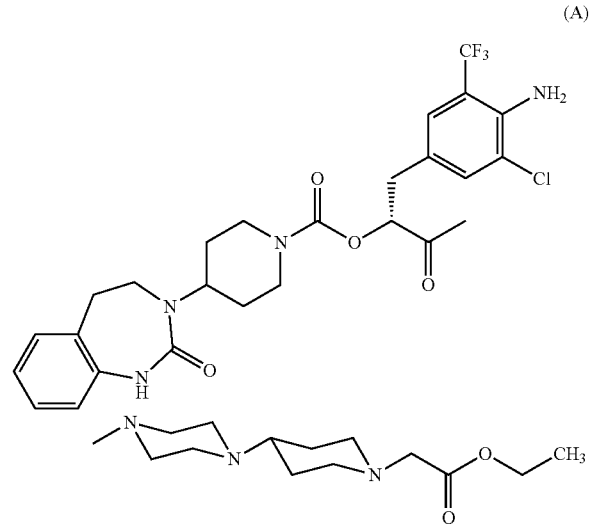

2 Claims, 9 Drawing Sheets

Figure 1: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1a) – polymorph 1.
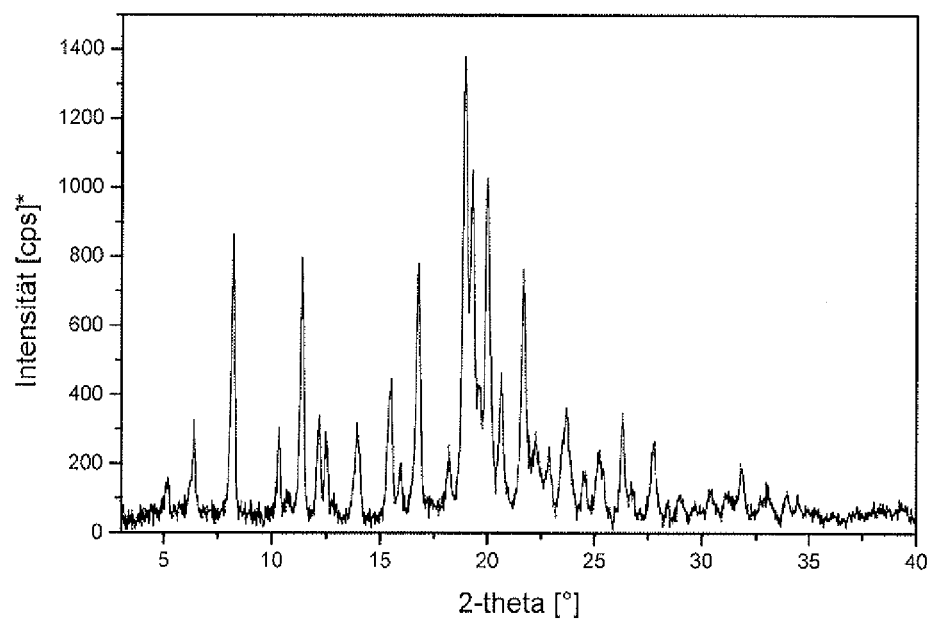
*) cps = counts per second
Intensität = intensity Figure 2: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1b) – polymorph 2.
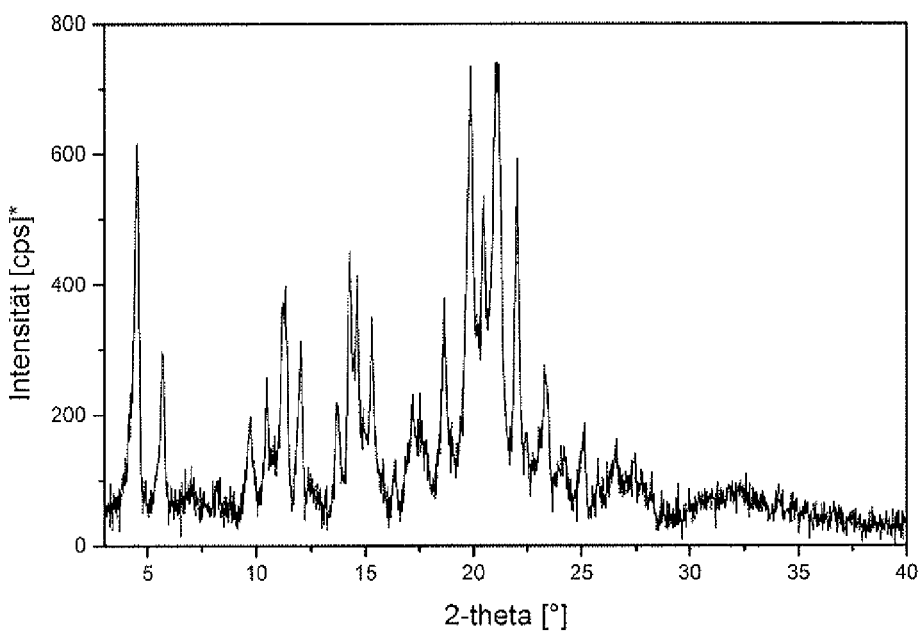
*) cps = counts per second
Intensität = intensity Figure 3: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1c) – polymorph 3.
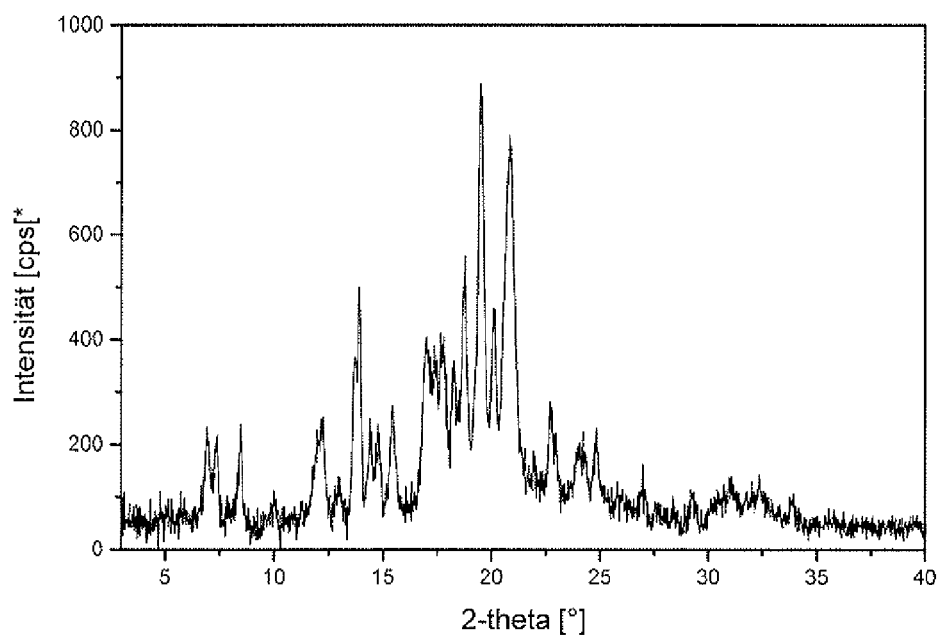
*) cps = counts per second
Intensität = intensity Figure 4: X-ray powder diffractogram of the crystalline compound 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate ethyl-hydrobromide (2).
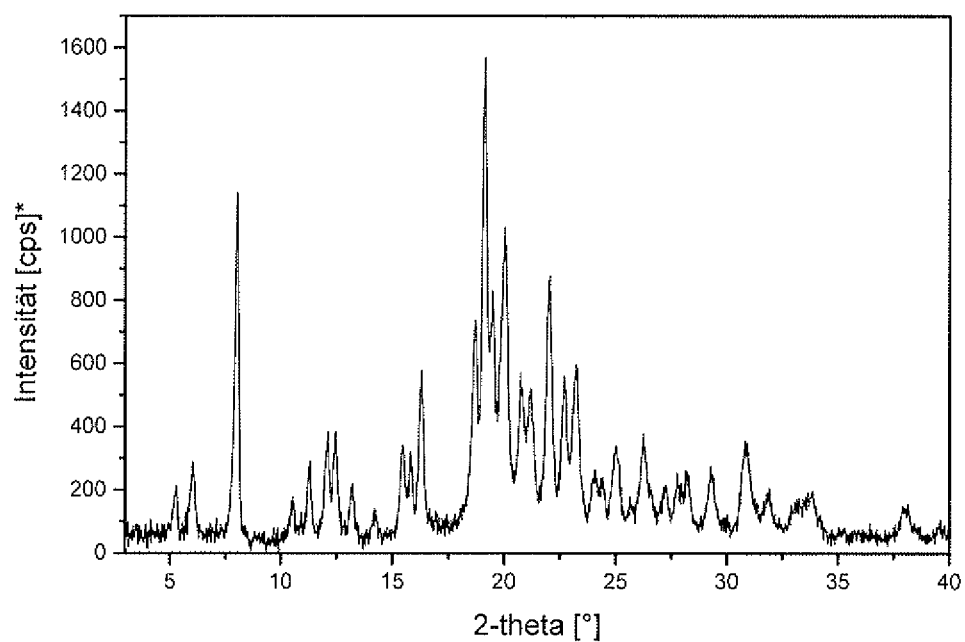
*) cps = counts per second
Intensität = intensity Figure 5: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate difumarate (3).
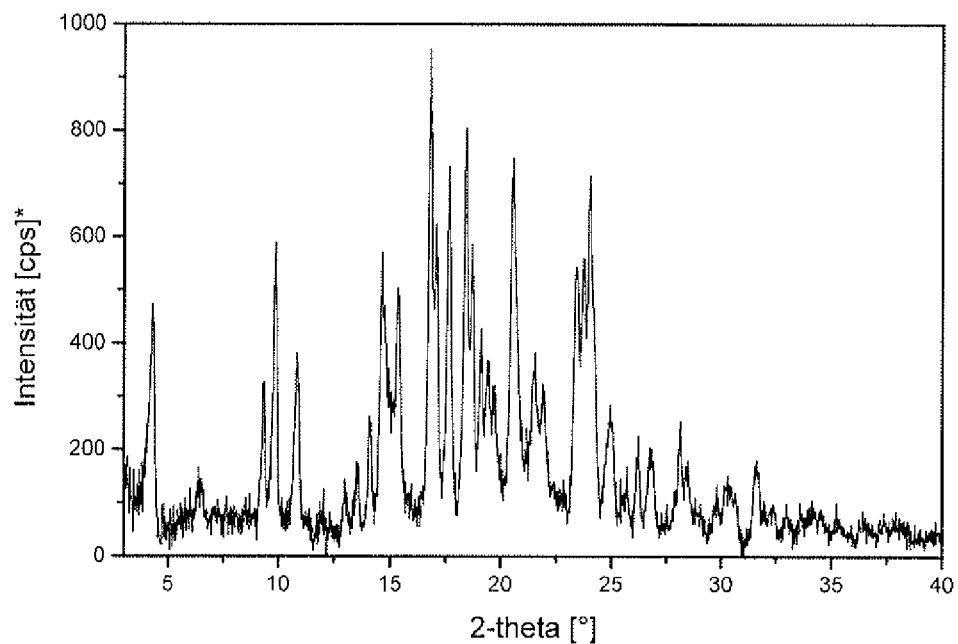
*) cps = counts per second
Intensität = intensity Figure 6: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate sulphate (4).
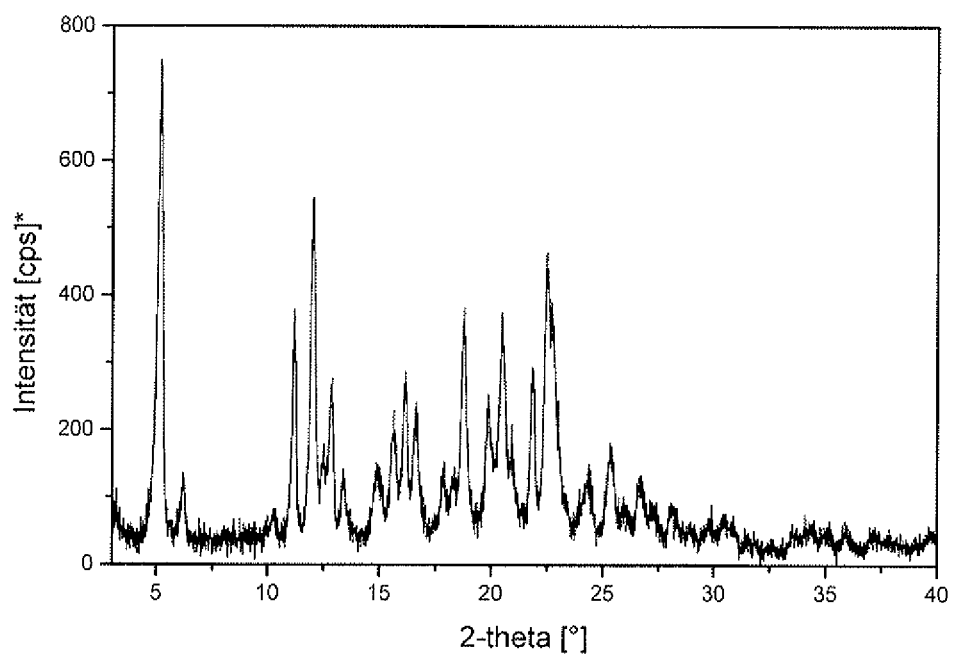
\*) cps = counts per second
Intensität = intensity Figure 7: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5a) – polymorph 1.
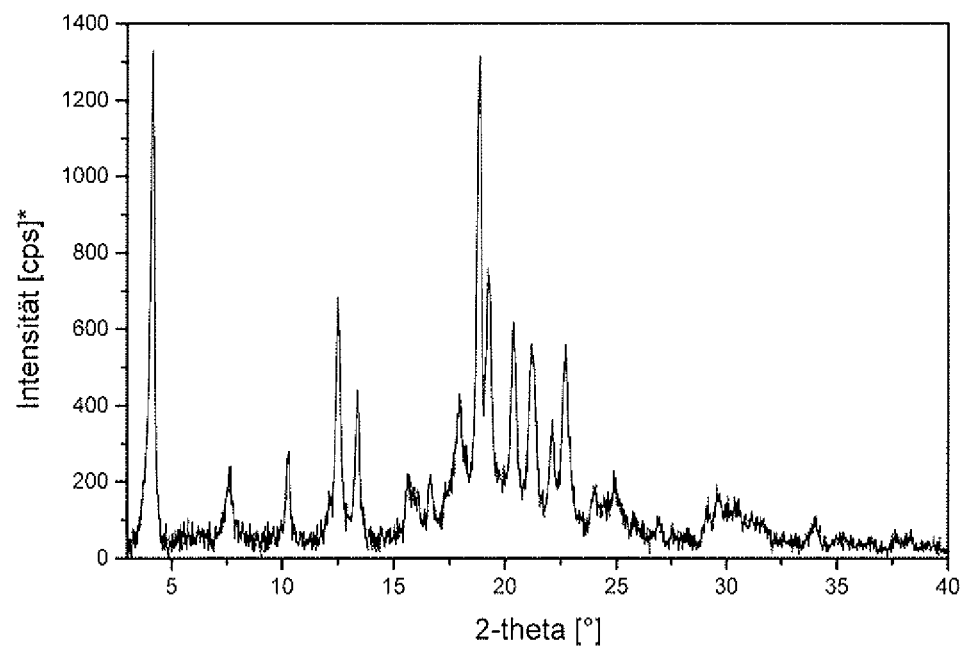
*) cps = counts per second
Intensität = intensity Figure 8: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5b) – polymorph 2.
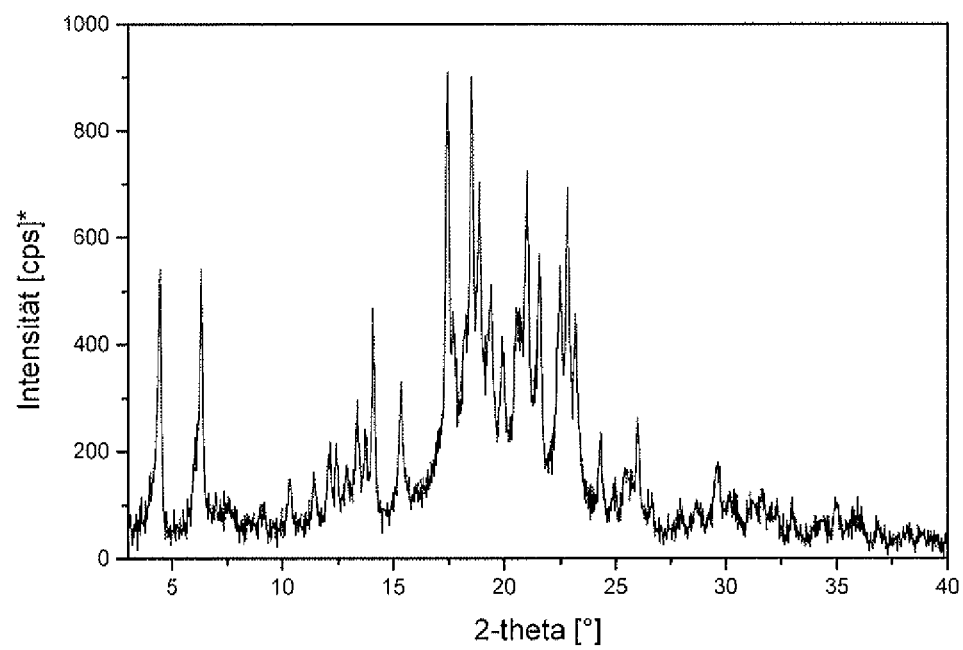
*) cps = counts per second
Intensität = intensity Figure 9: X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5c) – polymorph 3.
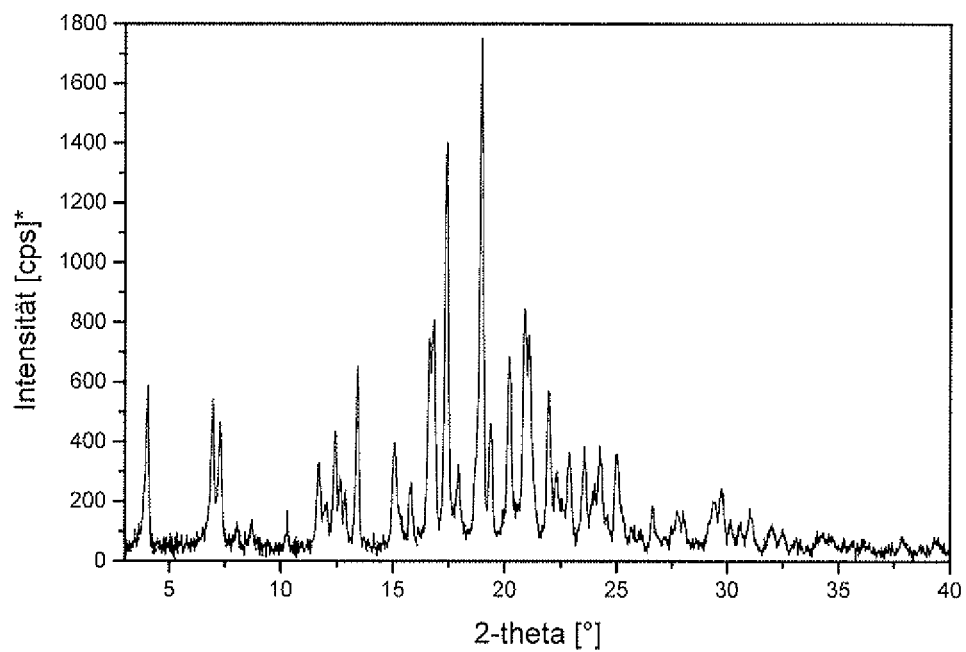
*) cps = counts per second
Intensität = intensity

CRYSTALLINE ETHYL 4-[4-[(2R)-3-[4-AMINO-3-CHLORO-5-(TRIFLUOROMETHYL)PHENYL]-1-OXO-2-[[[4-(1,2,4,5-TETRAHYDRO-2-OXO-3H-1,3-BENZODIAZEPIN-3-YL)-1-PIPERIDINYL]CARBONYL]OXY]PROPYL]-1-PIPERAZINYL]-PIPERIDINE-1-ACETATE DIFUMARATE

The present invention relates to the new salts AB of the base A

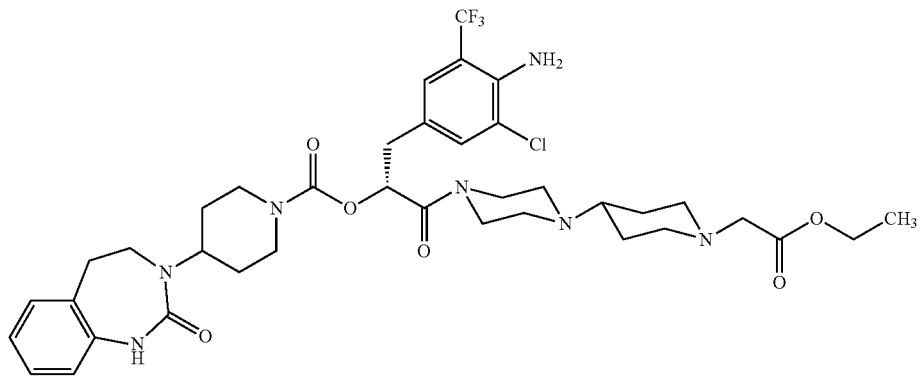

(A)

with a physiologically acceptable acid B that is selected from among hydrochloric acid, hydrobromic acid, sulphuric acid, fumaric acid and salicylic acid as well as the polymorphs and the corresponding solvates and hydrates.

BACKGROUND TO THE INVENTION

Technical Field

The present invention relates to CGRP antagonists which are in the form of stable crystalline derivatives and are suitable for the treatment of headaches, particularly for the treatment of migraine.

DETAILED DESCRIPTION OF THE INVENTION

The pharmacologically valuable properties of the compounds according to the invention constitute the basic prerequisite for effective use of the compound as a medicament. However, an active substance must also conform to additional requirements in order to be allowed to be used as a medicament. These parameters are to a large extent connected with the physicochemical nature of the active substance.

Without being restrictive, examples of these parameters are the stability of effect of the starting material under various environmental conditions, stability during production of the pharmaceutical formulation and stability in the final medicament compositions. The pharmaceutically active substance used for preparing the pharmaceutical compositions should therefore have a high stability which must be guaranteed even under different environmental conditions. This is absolutely essential to prevent the use of pharmaceutical compositions which contain, in addition to the actual active substance, breakdown products thereof, for example. In such cases the content of active substance in pharmaceutical formulations might be less than that specified.

The absorption of moisture reduces the content of pharmaceutically active substance on account of the weight gain caused by the uptake of water. Pharmaceutical compositions with a tendency to absorb moisture have to be protected from damp during storage, e.g. by the addition of suitable drying agents or by storing the medicament in a damp-proof environment. In addition, the uptake of moisture can reduce the content of pharmaceutically active substance during manufacture if the medicament is exposed to the environment without being protected from damp in any way. Preferably a pharmaceutically active substance should therefore have only limited hygroscopicity.

As the crystal modification of an active substance is important to the reproducible active substance content of a preparation, there is a need to clarify as far as possible any existing polymorphism of an active substance present in crystalline form. If there are different polymorphic modifications of an active substance care must be taken to ensure that the crystalline modification of the substance does not change in the pharmaceutical preparation later produced from it. Otherwise, this could have a harmful effect on the reproducible potency of the drug. Against this background, active substances characterised by only slight polymorphism are preferred.

Another criterion which may be of exceptional importance under certain circumstances depending on the choice of formulation or the choice of manufacturing process is the solubility of the active substance. If for example pharmaceutical solutions are prepared (e.g. for infusions) it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterised by high pharmacological potency but also satisfies the above-mentioned physicochemical requirements as far as possible.

Surprisingly, it has been found that the above problem is solved by the crystalline compounds according to the invention.

In a first aspect the present invention relates to the new salts AB of the base A

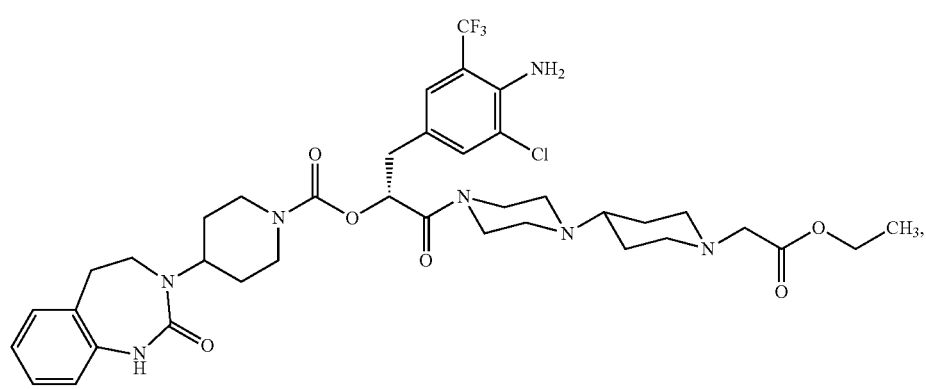

(A)

with a physiologically acceptable acid B, which is selected from among hydrochloric acid, hydrobromic acid, sulphuric acid, fumaric acid and salicylic acid as well as the polymorphs and the corresponding solvates and hydrates.

A preferred first object of the present invention relates to the above-mentioned salts in crystalline form.

In a second aspect the present invention relates to the following compounds:

(1) ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1), (2) ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrobromide (2), (3) ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate difumarate (3), (4) ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate sulphate (4), (5) ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5), the polymorphs, the solvates and the hydrates thereof.

The compounds according to the invention are characterised by a high degree of stability and are readily soluble in physiologically acceptable solvents.

In a preferred second aspect the present invention relates to the previously mentioned compounds in crystalline form.

The crystalline salts are in each case characterised by a characteristic melting point, which has been determined by Differential Scanning calorimetry (DSC: evaluated by means of the onset temperature or peak maximum, heating rate: 10° C./min). The values for the individual compounds listed in Table 1 were determined using a DSC 821 made by Mettler Toledo.

TABLE 1

Melting points of the crystalline salts according to the invention

| Number | melting point $T_{mp.}$ [° C.] |
|---|---|
| (1) | |
| (1a) polymorph 1 | 155 ± 5 (onset) |
| (1b) polymorph 2 | 163 ± 5 (onset) |
| (1c) polymorph 3 | 166 ± 5 (onset) |
| (2) | 150 ± 5 (onset) |
| (3) | 223 ± 5 (onset) |
| (4) | 206 ± 5 (onset) |
| (5) | |
| (5a) polymorph 1 | 109 ± 5 (onset) |
| (5b) polymorph 2 | 100 ± 5 (onset) |
| (5c) polymorph 3 | 104 ± 5 (onset) |

In a third aspect the present invention relates to the crystalline salts according to the invention, in each case characterised by their characteristic melting point. The melting point is dependent on the degree of purity of a compound and rises as the purity increases. This means that the compounds of the present invention may certainly have a melting point that is higher or lower than that specified.

More preferably, in a third aspect, the invention relates to the crystalline compound (1a) (polymorph 1), characterised by a melting point of $T_{mp.}=155\pm5°$ C.

More preferably, in a third aspect, the invention relates to the crystalline compound (1b) (polymorph 2), characterised by a melting point of $T_{mp.}=163\pm5°$ C.

More preferably, in a third aspect, the invention relates to the crystalline compound (1c) (polymorph 3), characterised by a melting point of $T_{mp.}=166\pm5°$ C.

More preferably, in a third aspect, the invention relates to the crystalline compound (2), characterised by a melting point of $T_{mp.}=150\pm5°$ C.

More preferably, in a third aspect, the invention relates to the crystalline compound (3), characterised by a melting point of $T_{mp.}=223\pm5°$ C.

More preferably, in a third aspect, the invention relates to the crystalline compound (4), characterised by a melting point of $T_{mp.}=206\pm5°$ C.

More preferably, in a third aspect, the invention relates to the crystalline compound (5a) (polymorph 1), characterised by a melting point of $T_{mp.}=109\pm5°$ C.

More preferably, in a third aspect, the invention relates to the crystalline compound (5b) (polymorph 2), characterised by a melting point of $T_{mp.}=100\pm5°$ C.

More preferably, in a third aspect, the invention relates to the crystalline compound (5c) (polymorph 3), characterised by a melting point of $T_{mp.}=104\pm5°$ C.

The crystalline forms of the individual salts according to the invention were investigated more closely by X-ray powder diffraction. The diagrams obtained are shown in FIGS. 1 to 5.

The following Tables 2 to 6 contain a compilation of the data obtained in the analyses carried out.

TABLE 2a

X-ray powder reflections and intensities (standardised) of compound (1a) - polymorph 1.

| d value [Å] | 2-theta [°] | relative intensity [%] |
|---|---|---|
| 16.98 | 5.20 | 8 |
| 13.77 | 6.41 | 20 |
| 10.74 | 8.23 | 61 |
| 8.56 | 10.32 | 18 |
| 7.76 | 11.40 | 54 |
| 7.25 | 12.19 | 22 |
| 7.08 | 12.50 | 17 |
| 6.35 | 13.94 | 21 |
| 5.72 | 15.48 | 28 |
| 5.55 | 15.95 | 11 |
| 5.28 | 16.79 | 54 |
| 4.88 | 18.17 | 14 |
| 4.69 | 18.91 | 100 |
| 4.60 | 19.27 | 74 |
| 4.53 | 19.58 | 28 |
| 4.44 | 19.98 | 74 |
| 4.30 | 20.63 | 31 |
| 4.10 | 21.68 | 52 |
| 3.99 | 22.25 | 18 |
| 3.89 | 22.86 | 15 |
| 3.75 | 23.68 | 24 |
| 3.63 | 24.52 | 10 |
| 3.53 | 25.21 | 14 |
| 3.39 | 26.31 | 22 |
| 3.21 | 27.75 | 16 |
| 3.08 | 28.99 | 5 |
| 2.93 | 30.43 | 6 |
| 2.81 | 31.81 | 11 |
| 2.64 | 33.97 | 5 |
| 2.60 | 34.47 | 5 |

TABLE 2b

X-ray powder reflections and intensities (standardised) of compound (1b) - polymorph 2.

| d value [Å] | 2-theta [°] | relative intensity [%] |
|---|---|---|
| 19.60 | 4.51 | 83 |
| 15.59 | 5.67 | 38 |
| 9.10 | 9.72 | 22 |
| 8.43 | 10.48 | 31 |
| 7.84 | 11.27 | 50 |
| 7.36 | 12.02 | 39 |
| 6.46 | 13.70 | 26 |
| 6.20 | 14.28 | 57 |
| 6.06 | 14.62 | 48 |
| 5.79 | 15.30 | 46 |
| 5.41 | 16.38 | 14 |
| 5.16 | 17.17 | 25 |
| 5.06 | 17.52 | 26 |
| 4.75 | 18.65 | 45 |
| 4.46 | 19.88 | 98 |
| 4.33 | 20.48 | 69 |
| 4.20 | 21.12 | 100 |
| 4.03 | 22.04 | 75 |
| 3.81 | 23.36 | 32 |
| 3.55 | 25.09 | 19 |
| 3.46 | 25.76 | 12 |
| 3.35 | 26.57 | 17 |
| 3.25 | 27.39 | 14 |
| 3.16 | 28.22 | 11 |

TABLE 2c

X-ray powder reflections and intensities (standardised) of compound (1c) - polymorph 3.

| d value [Å] | 2-theta [°] | relative intensity [%] |
|---|---|---|
| 18.43 | 4.79 | 7 |
| 12.71 | 6.95 | 22 |
| 12.00 | 7.36 | 20 |
| 10.44 | 8.46 | 24 |
| 8.85 | 9.99 | 6 |
| 7.37 | 12.00 | 21 |
| 7.23 | 12.23 | 24 |
| 6.83 | 12.96 | 13 |
| 6.37 | 13.90 | 54 |
| 6.14 | 14.41 | 22 |
| 6.12 | 14.45 | 21 |
| 5.99 | 14.79 | 24 |
| 5.73 | 15.45 | 28 |
| 5.20 | 17.03 | 42 |
| 5.10 | 17.39 | 39 |
| 5.01 | 17.68 | 42 |
| 4.98 | 17.80 | 43 |
| 4.85 | 18.27 | 37 |
| 4.73 | 18.76 | 56 |
| 4.55 | 19.52 | 100 |
| 4.41 | 20.12 | 50 |
| 4.26 | 20.83 | 87 |
| 4.05 | 21.93 | 17 |
| 3.91 | 22.72 | 28 |
| 3.70 | 24.03 | 19 |
| 3.58 | 24.84 | 24 |

TABLE 3

X-ray powder reflections and intensities (standardised) of compound (2).

| d value [Å] | 2-theta [°] | relative intensity [%] |
|---|---|---|
| 16.80 | 5.26 | 11 |
| 14.65 | 6.03 | 17 |
| 11.02 | 8.02 | 75 |
| 8.41 | 10.52 | 8 |
| 8.08 | 10.94 | 6 |
| 7.83 | 11.29 | 16 |
| 7.30 | 12.12 | 22 |
| 7.09 | 12.47 | 23 |
| 6.70 | 13.20 | 11 |
| 6.22 | 14.23 | 7 |
| 5.73 | 15.46 | 21 |
| 5.60 | 15.81 | 19 |
| 5.44 | 16.29 | 36 |
| 4.74 | 18.71 | 47 |
| 4.64 | 19.13 | 100 |
| 4.55 | 19.48 | 54 |
| 4.43 | 20.03 | 65 |
| 4.27 | 20.77 | 32 |
| 4.19 | 21.18 | 32 |
| 4.03 | 22.01 | 57 |
| 3.92 | 22.69 | 36 |

TABLE 3-continued

X-ray powder reflections and intensities (standardised) of compound (2).

| d value [Å] | 2-theta [°] | relative intensity [%] |
|---|---|---|
| 3.83 | 23.23 | 37 |
| 3.69 | 24.07 | 14 |
| 3.65 | 24.40 | 13 |
| 3.56 | 25.03 | 21 |
| 3.47 | 25.66 | 9 |
| 3.39 | 26.25 | 22 |
| 3.28 | 27.20 | 13 |
| 3.21 | 27.77 | 14 |
| 3.16 | 28.21 | 15 |
| 3.05 | 29.30 | 16 |
| 2.90 | 30.83 | 21 |
| 2.80 | 31.90 | 11 |

TABLE 4

X-ray powder reflections and intensities (standardised) of compound (3).

| d value [Å] | 2-theta [°] | relative intensity [%] |
|---|---|---|
| 20.53 | 4.30 | 52 |
| 13.74 | 6.43 | 17 |
| 9.46 | 9.34 | 36 |
| 8.97 | 9.85 | 64 |
| 8.16 | 10.83 | 40 |
| 6.81 | 12.99 | 13 |
| 6.54 | 13.53 | 17 |
| 6.28 | 14.10 | 28 |
| 6.04 | 14.66 | 62 |
| 5.76 | 15.38 | 55 |
| 5.27 | 16.81 | 100 |
| 5.19 | 17.08 | 65 |
| 5.02 | 17.65 | 78 |
| 4.82 | 18.40 | 89 |
| 4.74 | 18.70 | 64 |
| 4.64 | 19.10 | 43 |
| 4.56 | 19.43 | 39 |
| 4.50 | 19.70 | 33 |
| 4.32 | 20.55 | 80 |
| 4.19 | 21.20 | 22 |
| 4.13 | 21.51 | 38 |
| 4.05 | 21.91 | 35 |
| 3.80 | 23.41 | 61 |
| 3.74 | 23.74 | 61 |
| 3.70 | 24.01 | 76 |
| 3.56 | 24.96 | 28 |
| 3.50 | 25.44 | 11 |
| 3.46 | 25.73 | 14 |
| 3.39 | 26.23 | 20 |
| 3.32 | 26.82 | 21 |
| 3.17 | 28.13 | 24 |
| 3.14 | 28.44 | 18 |
| 2.99 | 29.83 | 11 |
| 2.93 | 30.44 | 11 |
| 2.83 | 31.63 | 17 |
| 2.77 | 32.32 | 8 |
| 2.71 | 32.98 | 8 |

TABLE 5

X-ray powder reflections and intensities (standardised) of compound (4).

| d value [Å] | 2-theta [°] | relative intensity [%] |
|---|---|---|
| 17.04 | 5.18 | 100 |
| 14.18 | 6.23 | 15 |

TABLE 5-continued

X-ray powder reflections and intensities (standardised) of compound (4).

| d value [Å] | 2-theta [°] | relative intensity [%] |
|---|---|---|
| 8.59 | 10.29 | 7 |
| 7.91 | 11.18 | 51 |
| 7.36 | 12.02 | 72 |
| 7.06 | 12.53 | 21 |
| 6.89 | 12.85 | 34 |
| 6.60 | 13.40 | 16 |
| 5.92 | 14.96 | 18 |
| 5.66 | 15.64 | 29 |
| 5.49 | 16.13 | 35 |
| 5.32 | 16.66 | 30 |
| 4.96 | 17.86 | 16 |
| 4.84 | 18.30 | 14 |
| 4.72 | 18.79 | 48 |
| 4.46 | 19.87 | 30 |
| 4.33 | 20.48 | 50 |
| 4.25 | 20.89 | 22 |
| 4.06 | 21.85 | 37 |
| 3.95 | 22.47 | 61 |
| 3.91 | 22.71 | 49 |
| 3.87 | 22.99 | 27 |
| 3.66 | 24.32 | 15 |
| 3.51 | 25.36 | 21 |
| 3.43 | 25.94 | 10 |
| 3.33 | 26.74 | 15 |
| 3.17 | 28.14 | 9 |
| 3.00 | 29.74 | 5 |
| 2.93 | 30.46 | 7 |

TABLE 6a

X-ray powder reflections and intensities (standardised) of compound (5a) - polymorph 1.

| d value [Å] | 2-theta [°] | relative intensity [%] |
|---|---|---|
| 21.28 | 4.15 | 100 |
| 11.62 | 7.60 | 14 |
| 8.61 | 10.27 | 20 |
| 7.32 | 12.09 | 11 |
| 7.07 | 12.51 | 49 |
| 6.61 | 13.38 | 31 |
| 5.65 | 15.68 | 15 |
| 5.32 | 16.64 | 14 |
| 4.94 | 17.94 | 30 |
| 4.71 | 18.83 | 98 |
| 4.61 | 19.26 | 56 |
| 4.35 | 20.38 | 45 |
| 4.19 | 21.20 | 41 |
| 4.02 | 22.12 | 25 |
| 3.92 | 22.69 | 39 |
| 3.70 | 24.03 | 11 |
| 3.58 | 24.88 | 16 |
| 3.01 | 29.62 | 12 |
| 2.63 | 34.01 | 7 |

TABLE 6b

X-ray powder reflections and intensities (standardised) of compound (5b) - polymorph 2.

| d value [Å] | 2-theta [°] | relative intensity [%] |
|---|---|---|
| 19.92 | 4.43 | 57 |
| 13.93 | 6.34 | 55 |
| 8.55 | 10.34 | 14 |
| 7.74 | 11.43 | 15 |
| 7.29 | 12.13 | 20 |

TABLE 6b-continued

X-ray powder reflections and intensities (standardised) of compound (5b) - polymorph 2.

| d value [Å] | 2-theta [°] | relative intensity [%] |
|---|---|---|
| 7.13 | 12.40 | 20 |
| 6.87 | 12.88 | 16 |
| 6.63 | 13.35 | 27 |
| 6.46 | 13.71 | 21 |
| 6.28 | 14.08 | 49 |
| 5.77 | 15.33 | 33 |
| 5.09 | 17.42 | 100 |
| 5.01 | 17.70 | 46 |
| 4.87 | 18.22 | 47 |
| 4.78 | 18.53 | 97 |
| 4.70 | 18.88 | 72 |
| 4.58 | 19.37 | 53 |
| 4.45 | 19.93 | 44 |
| 4.31 | 20.60 | 50 |
| 4.23 | 21.00 | 75 |
| 4.12 | 21.56 | 60 |
| 3.95 | 22.47 | 55 |
| 3.89 | 22.81 | 72 |
| 3.83 | 23.19 | 47 |
| 3.66 | 24.31 | 22 |
| 3.57 | 24.95 | 13 |
| 3.50 | 25.43 | 15 |
| 3.43 | 25.97 | 26 |
| 3.35 | 26.63 | 11 |
| 3.11 | 28.70 | 8 |
| 3.01 | 29.62 | 16 |
| 2.83 | 31.63 | 10 |
| 2.71 | 33.01 | 10 |
| 2.56 | 34.98 | 8 |

TABLE 6c

X-ray powder reflections and intensities (standardised) of compound (5c) - polymorph 3.

| d value [Å] | 2-theta [°] | relative intensity [%] |
|---|---|---|
| 21.93 | 4.03 | 31 |
| 12.72 | 6.94 | 29 |
| 12.13 | 7.28 | 25 |
| 10.99 | 8.04 | 6 |
| 10.17 | 8.69 | 6 |
| 8.58 | 10.30 | 7 |
| 7.56 | 11.70 | 17 |
| 7.12 | 12.42 | 24 |
| 7.00 | 12.64 | 16 |
| 6.87 | 12.88 | 12 |
| 6.60 | 13.41 | 36 |
| 5.87 | 15.08 | 22 |
| 5.61 | 15.80 | 13 |
| 5.32 | 16.66 | 43 |
| 5.27 | 16.82 | 45 |
| 5.09 | 17.40 | 79 |
| 4.94 | 17.94 | 17 |
| 4.68 | 18.96 | 100 |
| 4.58 | 19.37 | 26 |
| 4.46 | 19.90 | 8 |
| 4.39 | 20.20 | 39 |
| 4.25 | 20.89 | 49 |
| 4.21 | 21.07 | 43 |
| 4.05 | 21.94 | 32 |
| 3.98 | 22.30 | 16 |
| 3.88 | 22.88 | 20 |
| 3.77 | 23.56 | 20 |
| 3.66 | 24.27 | 20 |
| 3.56 | 25.01 | 20 |
| 3.35 | 26.62 | 9 |
| 3.21 | 27.75 | 8 |
| 3.18 | 28.02 | 8 |
| 3.04 | 29.37 | 10 |
| 3.00 | 29.73 | 12 |
| 2.96 | 30.16 | 6 |
| 2.92 | 30.61 | 5 |
| 2.88 | 31.03 | 8 |
| 2.79 | 32.04 | 5 |
| 2.75 | 32.51 | 4 |

In the above Tables 2 to 6 the value "2Θ[°]" denotes the diffraction angle in degrees and the value "d (hkl) [Å]" denotes the intervals in Å measured between the lattice planes.

The X-ray powder diagrams of the compounds (1), and (5) were recorded within the scope of the present invention using a STOE-STADI P diffractometer in transmission mode, equipped with a site-sensitive detector (SSD) and a Cu anode as the X-ray source with filtered CuK$_\alpha$ radiation ($\square$=1.54056 Å, 40 kV, 40 mA).

According to the findings shown in Table 2a the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate-hydrochloride (1a; polymorph 1), characterised in that in the X-ray powder diagram it has, inter alia, the characteristic values d=10.74 Å, 7.76 Å, 5.28 Å, 4.69 Å, 4.60 Å, 4.44 Å and 4.10 Å.

According to the findings shown in Table 2b the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1b; polymorph 2), characterised in that in the X-ray powder diagram it has, inter alia, the characteristic values d=19.60 Å, 7.84 Å, 6.20 Å, 4.46 Å, 4.33 Å, 4.20 Å and 4.03 Å.

According to the findings shown in Table 2c the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1c; polymorph 3), characterised in that in the X-ray powder diagram it has, inter alia, the characteristic values d=6.37 Å, 5.20 Å, 5.01 Å, 4.98 Å, 4.73 Å, 4.55 Å, 4.41 Å and 4.26 Å.

According to the findings shown in Table 3 the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrobromide (2), characterised in that in the X-ray powder diagram it has, inter alia, the characteristic values d=11.02 Å, 4.74 Å, 4.64 Å, 4.55 Å, 4.43 Å and 4.03 Å.

According to the findings shown in Table 4 the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate difumarate (3), characterised in that in the X-ray powder diagram it has, inter alia, the characteristic values d=20.53 Å, 8.97 Å, 6.04 Å, 5.76 Å, 5.27 Å, 5.19 Å, 5.02 Å, 4.82 Å, 4.74 Å, 4.32 Å, 3.80 Å, 3.74 Å and 3.70 Å.

According to the findings shown in Table 5 the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate sulphate (4), characterised in that in the X-ray powder diagram it has, inter alia, the characteristic values d=17.04 Å, 7.91 Å, 7.36 Å, 4.72 Å, 4.33 Å, 3.95 Å and 3.91 Å.

According to the findings shown in Table 6a the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5a, polymorph 1), characterised in that in the X-ray powder diagram it has, inter alia, the characteristic values d=21.28 Å, 7.07 Å, 4.71 Å, 4.61 Å, 4.35 Å and 4.19 Å.

According to the findings shown in Table 6b the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5b, polymorph 2), characterised in that in the X-ray powder diagram it has, inter alia, the characteristic values d=19.92 Å, 13.93 Å, 5.09 Å, 4.78 Å, 4.70 Å, 4.58 Å, 4.31 Å, 4.23 Å, 4.12 Å, 3.95 Å and 3.89 Å.

According to the findings shown in Table 6c the present invention relates to crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5c, polymorph 3), characterised in that in the X-ray powder diagram it has, inter alia, the characteristic values d=5.32 Å, 5.27 Å, 5.09 Å, 4.68 Å, 4.25 Å and 4.21 Å.

Methods of Preparation

The compounds of general formula I are prepared using methods known in principle. The methods described in the "*Handbook of Pharmaceutical Salts*" (Eds. P. Heinrich Stahl, Camille G. Wermuth, Wiley-VHC 2002) have proved particularly suitable.

As an example of a preferred method of preparation according to the present invention the preparation of the crystalline salt 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate ethyl-difumarate (3) according to the invention will be described in more detail, comprising the following steps:

(a) mixing the base 2-oxoethyl (1R)-4-(1,2,4,5-tetrahydro-2-oxo-3H-1,3-benzodiazepin-3-yl)-1-[[4-amino-3-chloro-5-trifluoro-phenyl]methyl]-2-[4-(1-piperazinyl)-ethyl 1-piperidinoacetate-]-1-piperidinecarboxylate with a polar solvent at ambient temperature and subsequently heating the reaction mixture;
(b) adding a mixture of fumaric acid in a polar solvent to the reaction mixture obtained under (a);
(c) slowly cooling the reaction mixture obtained under (b), isolating and drying the salt formed and
(d) optionally recrystallising the salt (R)-1-(4-amino-3-chloro-5-trifluoromethyl-benzyl]-2-[4-(1-ethoxycarbonylmethyl-piperidin-4-yl)-piperazin-1-yl]-2-oxy-ethyl 4-(2-oxo-1,2,4,5-tetrahydro-1,3-benzodiazepin-3-yl)-piperidine-1-carboxylate difumarate, obtained under (c), from a suitable solvent.

The preparation of the compound 2-oxoethyl (1R)-4-(1,2,4,5-tetrahydro-2-oxo-3H-1,3-benzodiazepin-3-yl)-1-[[4-amino-3-chloro-5-trifluoro-phenyl]methyl]-2-[4-(1-piperazinyl)-ethyl 1-piperidinoacetate]-1-piperidinecarboxylate of formula 2

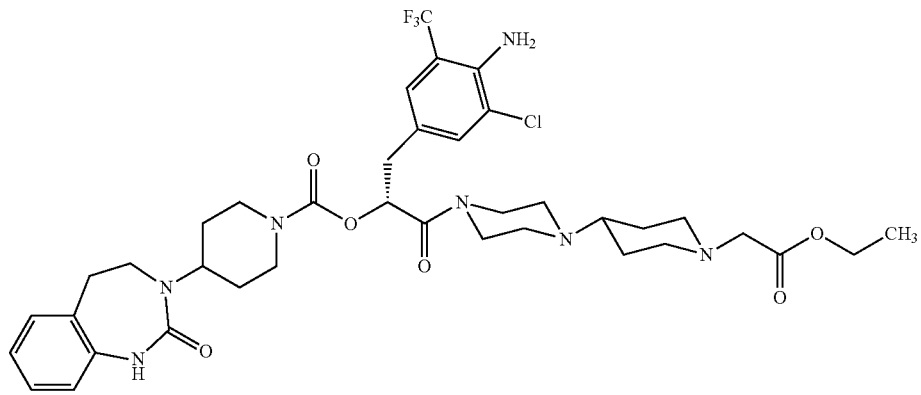 [SMILES: CCOC(=O)CN1CCC(N2CCN(C(=O)[C@@H](Cc3cc(Cl)c(N)c(C(F)(F)F)c3)OC(=O)N3CCC(N4CCc5ccccc5NC4=O)CC3)CC2)CC1]

used as starting material is described in International Patent Application PCT/EP2006/065314.

The polar solvent used in steps (a) and (b) according to the invention may be methanol, ethanol, propanol, isopropanol or a mixture of these solvents, while ethanol or isopropanol or a 1:1 mixture of ethanol and isopropanol according to the invention may preferably be used. Preferably the same solvent is used in step (a) and (b).

The solvent in step (a) may be used in an amount of 2 to 4 L/mol of the base used, preferably in an amount of 3 to 4 L/mol of the base used.

The reaction mixture formed in step (a) is then heated to the boiling temperature of the solvent used.

The solvent in step (b) may be used in an amount of 1 to 3 L/mol of the fumaric acid used, preferably in an amount of 2 to 3 L/mol of the fumaric acid used.

According to the invention it is particularly preferred to use ethanol as the solvent in steps (a) and (b).

According to the invention ethanol, propanol, isopropanol or a mixture of these solvents may be used as the solvent in step (c).

The preparation process described can also be used on an industrial scale for producing large quantities of substance.

In another aspect the present invention relates to the use of the new salts as medicaments in view of their pharmaceutical efficacy.

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS), inflammatory bowel syndrome. In addition, the compounds according to the invention have a general pain-relieving effect. The symptoms of menopausal hot flushes caused by vasodilatation and increased blood flow in estrogen-deficient women and hormone-treated patients with prostate carcinoma and castrated men are favourably affected by the present use of the CGRP antagonists in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for treating irritable bowel syndrome (IBS) and for the preventive and acute-therapeutic treatment of hot flushes in estrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, one to three times a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiinflammatories, corticosteroids, calcium antagonists, 5-$HT_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptyline, imipramine, venlafaxine, lidocaine or diltiazem and other 5-$HT_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. MGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. Sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more of the compounds according to the invention.

It is particularly preferable if the compounds of formula I are administered orally, and it is particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds according to the invention are administered by inhalation, particularly preferably if they are administered once or twice a day. For this purpose, the compounds according to the invention have to be made available in forms suitable for inhalation. Inhalable preparations include inhalable powders, propellant-containing metered-dose aerosols or propellant-free inhalable solutions, which are optionally present in admixture with conventional physiologically acceptable excipients.

EXPERIMENTAL SECTION

Example 1

Ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]-propyl]-1-piperazinyl]-piperidine-1-acetate Hydrochloride (1)

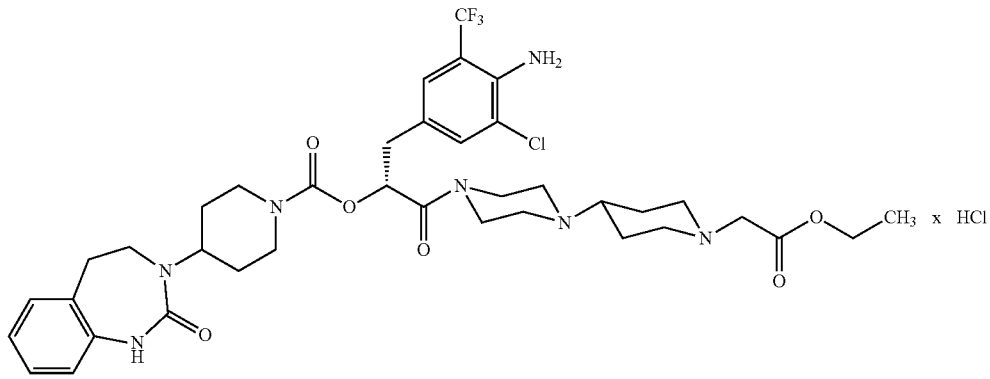 [SMILES: CCOC(=O)CN1CCC(N2CCN(C(=O)[C@@H](Cc3cc(Cl)c(N)c(C(F)(F)F)c3)OC(=O)N3CCC(N4CCc5ccccc5NC4=O)CC3)CC2)CC1 ; Cl]

(1a) Polymorph 1; Form A 250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol) are dissolved in 2.5 ml 1-propanol at ambient temperature. The solution is heated to 80° C. and combined with 98 µL isopropanolic hydrochloric acid (3.2 Mol/l, 0.316 mmol). The temperature is lowered by 5° C. every 30 minutes. The suspension formed is stirred for 12 hours at ambient temperature. The solid formed is filtered off, washed with a little 1-propanol and dried for 12 hours at 35° C.

Yield: 60 mg (23% of theory)

(1b) Polymorph 2; Form B 250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol) are dissolved in 2.5 ml ethyl acetate at ambient temperature. The solution is heated to 80° C. and combined with 98 µL isopropanolic hydrochloric acid (3.2 Mol/l, 0.316 mmol). The temperature is lowered by 5° C. every 30 minutes. The suspension formed is stirred for 12 hours at ambient temperature. The solid formed is filtered off, washed with a little ethyl acetate and dried for 12 hours at 35° C.

Yield: 180 mg (69% of theory)

(1c) Polymorph 3; Form C 250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol) of are dissolved in 2.5 ml of tetrahydrofuran at ambient temperature. The solution is heated to 80° C. and combined with 98 µL isopropanolic hydrochloric acid (3.2 Mol/l, 0.316 mmol). The temperature is lowered by 5° C. every 30 minutes. The suspension formed is stirred for 12 hours at ambient temperature. The solid formed is filtered off, washed with a little tetrahydrofuran and dried for 12 hours at 35° C.

Yield: 200 mg (74% of theory)

Example 2

Ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]-propyl]-1-piperazinyl]-piperidine-1-acetate Hydrobromide (2)

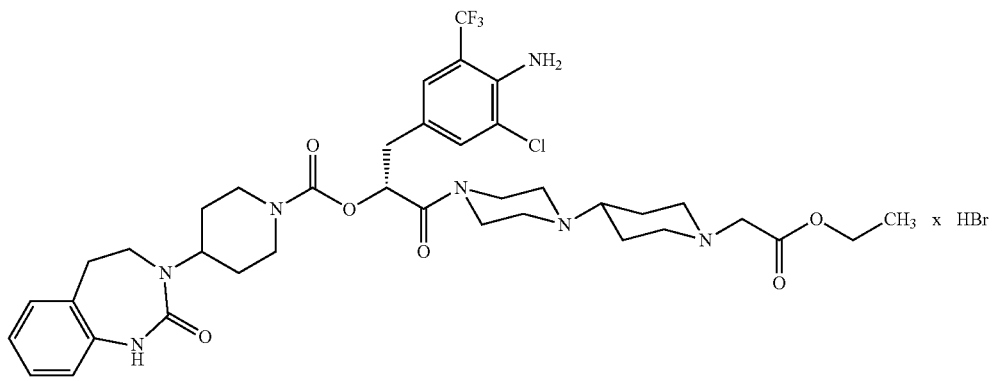 [SMILES: CCOC(=O)CN1CCC(N2CCN(C(=O)[C@@H](Cc3cc(Cl)c(N)c(C(F)(F)F)c3)OC(=O)N3CCC(N4CCc5ccccc5NC4=O)CC3)CC2)CC1 ; Br]

300 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.379 mmol) of are dissolved in 3 ml isopropanol at ambient temperature and combined with 75.4 µL hydrobromic acid (30% in glacial acetic acid, 0.379 mmol), whereupon a sticky precipitate is immediately formed. The suspension is heated to 100° C., whereupon the precipitate formed goes back into solution. The solution is slowly cooled to ambient temperature. The solid formed is filtered off, washed with a little isopropanol and dried for 12 hours at 40° C.

Yield: 200 mg (61% of theory)

Example 3.1

Ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate Difumarate (3)

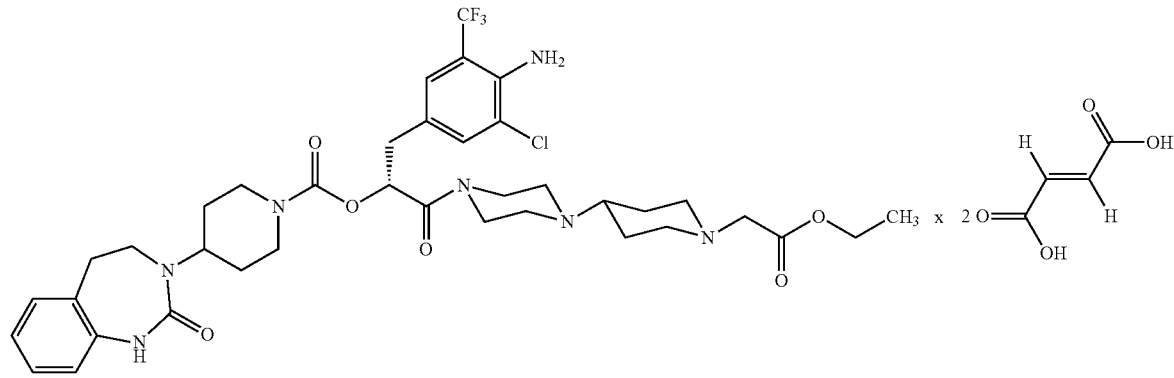

250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol) of are dissolved in 1 ml of ethanol at ambient temperature. The solution is heated to 80° C. and combined with a solution of 73 mg fumaric acid (0.631 mmol) in 2 ml of ethanol. The temperature is lowered by 5° C. every 30 minutes. The suspension formed is stirred for 12 hours at ambient temperature. The solid formed is filtered off, washed with ethanol and dried for 12 hours at 35° C.

Yield: 270 mg (84% of theory)

Example 3.2

Ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate Difumarate (3)

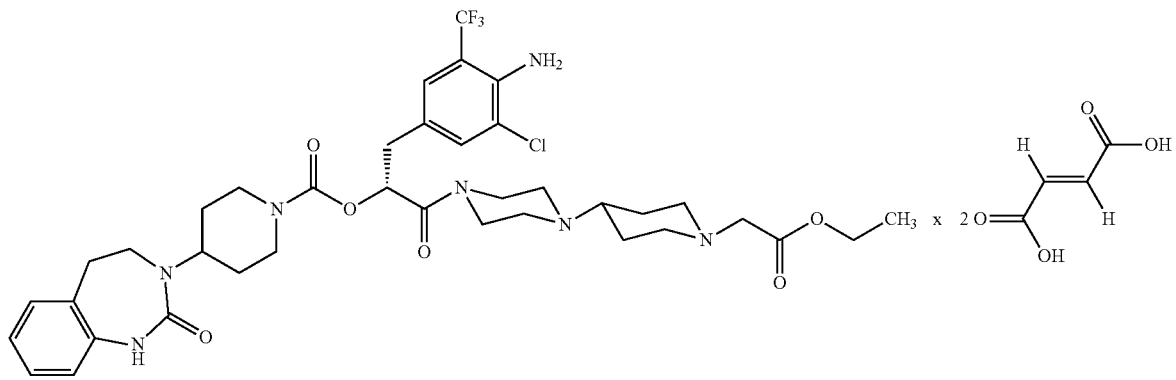

2.31 kg (2.92 mol) 2-oxoethyl (1R)-4-(1,2,4,5-tetrahydro-2-oxo-3H-1,3-benzodiazepin-3-yl)-1-[[4-amino-3-chloro-5-trifluoro-phenyl]methyl]-2-[4-(1-piperazinyl)-ethyl-1-piperidinoacetate]-1-piperidinecarboxylate were dissolved in 10 L ethanol and refluxed. Then a solution of 0.68 kg (5.86 mol) fumaric acid in 13 L ethanol was metered in and the mixture was refluxed for about another 30 minutes with stirring. Within 6 hours the mixture was cooled to 20° C., and the product was separated off and dried.

Yield: 2.57 kg (85% of theory)
ee value: 97.9%
melting point: 223° C.

Example 4

Ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate Sulphate (4)

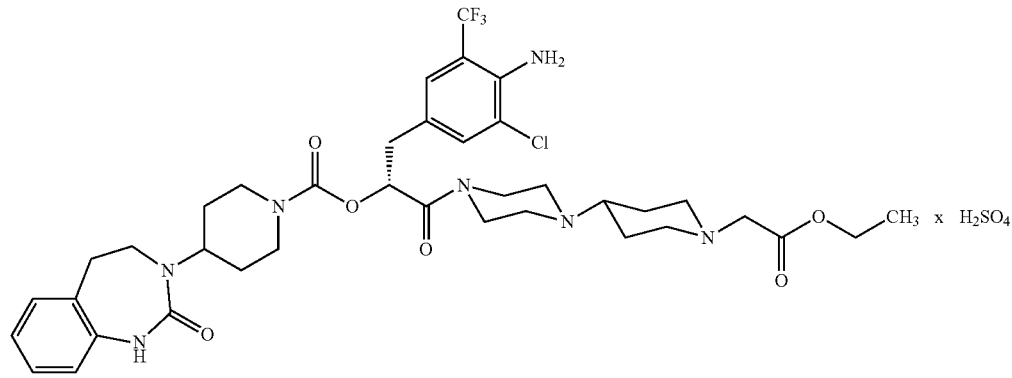

250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol) are dissolved in 2.5 ml of ethanol at ambient temperature. The solution is heated to 80° C. and combined with 46.8 μl aqueous sulphuric acid (48%), whereupon a granular precipitate is immediately formed. The temperature is lowered by 5° C. every 30 minutes. The suspension formed is stirred for 12 hours at ambient temperature. The solid formed is filtered off, washed with ethanol and dried for 12 hours at 40° C.

Yield: 130 mg (46% of theory)

Example 5

Ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate Salicylate (5)

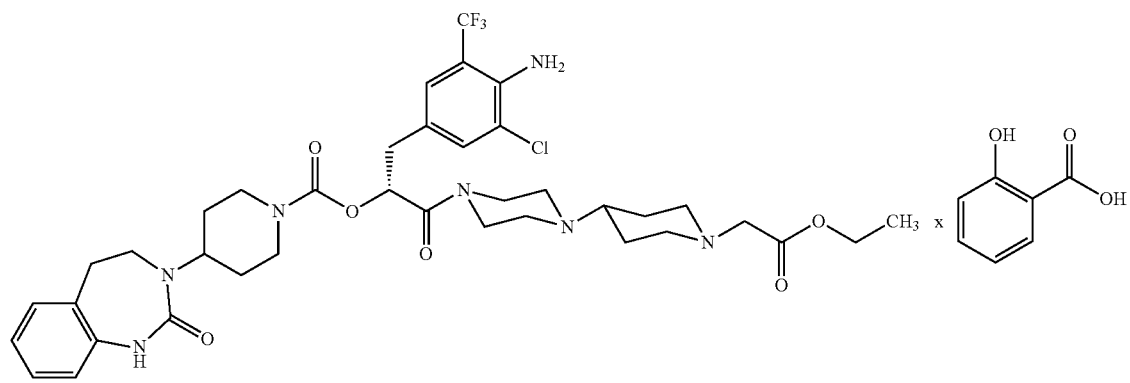 [SMILES: CCOC(=O)CN1CCC(N2CCN(C(=O)[C@@H](Cc3cc(Cl)c(N)c(C(F)(F)F)c3)OC(=O)N3CCC(N4CCc5ccccc5NC4=O)CC3)CC2)CC1 ; O=C(O)c1ccccc1O]

(5a) Polymorph 1; Form A 250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol) are dissolved in 1.5 ml of tetrahydrofuran at ambient temperature. The solution is heated to 80° C. and combined with a solution of 43 mg salicylic acid (0.361 mmol) is in 0.5 ml of tetrahydrofuran. The temperature is lowered by 5° C. every 30 minutes. The suspension formed is stirred for 12 hours at ambient temperature. The solid formed is filtered off, washed with a little tetrahydrofuran and dried for 12 hours at 35° C.

Yield: 100 mg (34% of theory)

(5b) Polymorph 2; Form B 250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol)

are dissolved in 1.5 ml dioxane at ambient temperature. The solution is heated to 80° C. and combined with a solution of 43 mg salicylic acid (0.361 mmol) in 0.5 ml dioxane. The temperature is lowered by 5° C. every 30 minutes. The suspension formed is stirred for 12 hours at ambient temperature. The solid formed is filtered off, washed with a little dioxane and dried for 12 hours at 35° C.

Yield: 190 mg (65% of theory)

(5c) Polymorph 3; Form C 250 mg ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate (0.316 mmol) are dissolved in 1.5 ml of ethanol at ambient temperature. The solution is heated to 80° C. and combined with a solution of 43 mg salicylic acid (0.361 mmol) in 1.5 ml of ethanol. The temperature is lowered by 5° C. every 30 minutes. Then the solution is stirred for 12 hours at ambient temperature. As no precipitate has formed, the solvent is distilled off and the residue is dissolved in 2.5 ml methylisobutylketone at 80° C. The temperature is lowered by 5° C. every 30 minutes. Then the solution is stirred for 12 hours at ambient temperature. Then the solution is stirred for a further 24 hours in the open vessel during which time the solvent evaporates. The resultant solid is filtered off, washed with methylisobutylketone and dried for 12 hours at 35° C.

Yield: 190 mg (65% of theory)

BRIEF DESCRIPTION OF THE FIGURES

FIG. 1 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1a; polymorph 1).

FIG. 2 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1b; polymorph 2).

FIG. 3 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrochloride (1c; polymorph 3).

FIG. 4 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate hydrobromide (2).

FIG. 5 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate difumarate (3).

FIG. 6 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate sulphate (4).

FIG. 7 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5a; polymorph 1).

FIG. 8 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5b; polymorph 2).

FIG. 9 shows the X-ray powder diffractogram of the crystalline compound ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate salicylate (5c; polymorph 3).

The invention claimed is:

1. Crystalline ethyl 4-[4-[(2R)-3-[4-amino-3-chloro-5-(trifluoromethyl)phenyl]-1-oxo-2-[[[4-(1,2,4,5-tetrahydro-2-oxo-3H-1,3-benzodiazepin-3-yl)-1-piperidinyl]carbonyl]oxy]propyl]-1-piperazinyl]-piperidine-1-acetate sulphate (3), characterised in that in the X-ray powder diagram it has, inter alia, the characteristic values d=20.53 Å, 8.97 Å, 6.04 Å, 5.76 Å, 5.27 Å, 5.19 Å, 5.02 Å, 4.82 Å, 4.74 Å, 4.32 Å, 3.80 Å, 3.74 Å and 3.70 Å.

2. A pharmaceutical composition containing a compound according to claim 1 together with one or more inert carriers and/or diluents.

* * * * *